Figure 1:
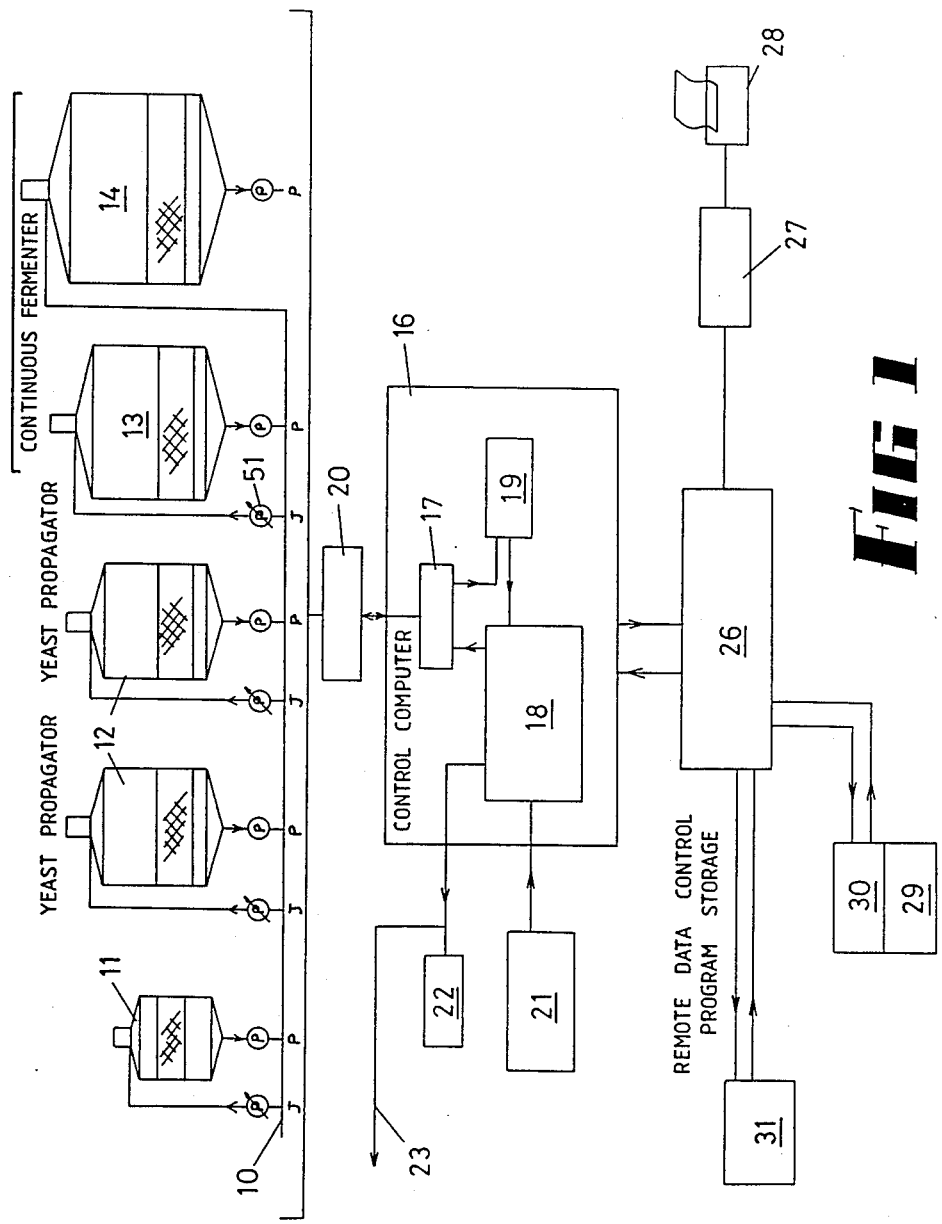

United States Patent [19]
Whitford

[11] Patent Number: 4,856,421
[45] Date of Patent: Aug. 15, 1989

[54] COMPUTER-CONTROLLED FERMENTATION MEANS FOR WINES

[75] Inventor: Darryl R. Whitford, Rosedale, Australia

[73] Assignee: S. Smith & Son Pty. Ltd., Angaston, Australia

[21] Appl. No.: 178,916

[22] Filed: Dec. 29, 1987

[30] Foreign Application Priority Data

May 2, 1986 [AU] Australia .............................. PH5719
May 1, 1987 [WO] World Int. Prop.
O. ........................ PCT/AU87/00126

[51] Int. Cl.⁴ ............................................. C12M 1/36
[52] U.S. Cl. ...................................... 99/276; 99/277.2
[58] Field of Search ....................... 99/276, 277, 277.1, 99/277.2, 278; 435/3, 4; 426/13, 14, 11

[56] References Cited
U.S. PATENT DOCUMENTS 4,424,559  1/1984  Lorincz ................................... 435/3
4,773,315  9/1988  Enenkel ................................. 99/277

FOREIGN PATENT DOCUMENTS 0089225  9/1983  European Pat. Off. .
1434613  5/1976  United Kingdom .

*Primary Examiner*—Robert W. Jenkins
*Attorney, Agent, or Firm*—Rodman & Rodman

[57] ABSTRACT

In the production of wine it is desireable that yeast propagation should remain substantially constant during fermentation and the wine to yeast propagation is normally cyclic. A computer controls functions between limits which are set both for Baume and cell count in a continuous fermenting tank. A Baume sensing means (for example a specific gravity sensing means) and a turbidity sensing means (for example a nephelometer sensor) sense the contents of the continuous fermenting tank. A pump pumps yeast from a yeast propagating tank in response to the requirements of the continuous fermenting tank. A second pump pumps partly fermented wine from the continuous fermenting tank into a buffer tank.

13 Claims, 3 Drawing Sheets

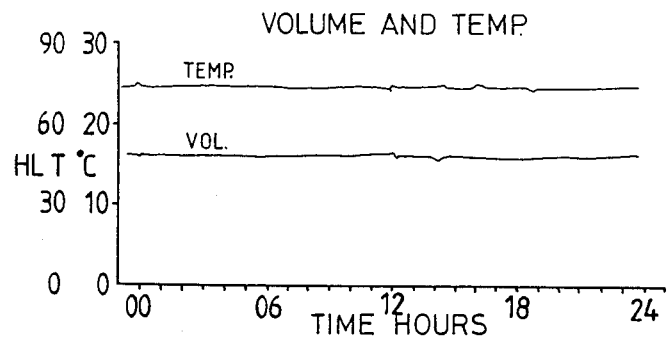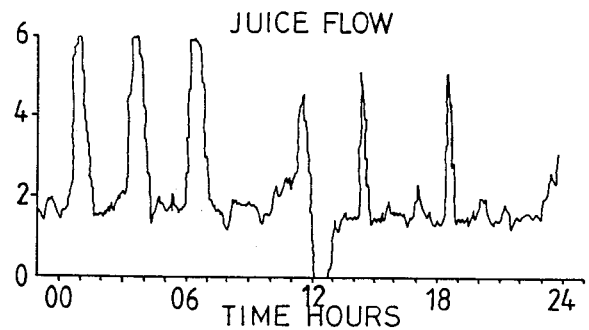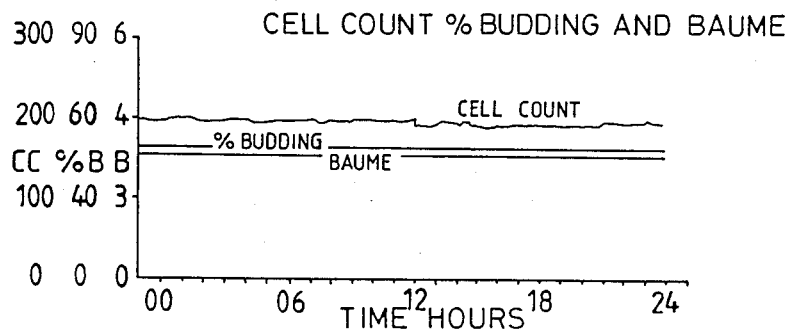
FIG 3

COMPUTER-CONTROLLED FERMENTATION MEANS FOR WINES

This invention relates to both means for and method of control of fermentation in the preparation of alcoholic beverages, for example wines.

When wines are produced according to prior art methods, crushed grape juice is firstly placed within a tank, and yeast is added, the yeast cells working on the grape sugar during the fermentation process, producing alcohol, heat and carbon-dioxide. Yeast growth is sensitive to temperature and the amount of available sugar.

This is essentially a batch type process, and is normally subject to wide variations of sugar content and yeast cell content during at least the initial stages of fermentation, and these variations are normally regarded as very difficult to control. Such variations can have a deleterious effect on wine quality and consistency.

The main object of this invention is to improve the fermentation control, and reduce the variations which occur under ordinary conditions, thereby improving the wine quality. The invention also extends to production of other alcoholic beverages.

In one embodiment of the invention, means for controlling fermentation of sugar solution in the production of an alcoholic beverage comprise:

(a) a yeast propagating tank;
(b) a continuous fermenting tank;
(c) a first pump having an input conduit connected to a source of sugar solution and an output conduit connected to the continuous fermenting tank;
(d) a second pump having an input conduit connected to an outlet of the continuous fermenting tank;
(e) Baume sensing means and yeast concentration sensing means in communication with the contents of the continuous fermenting tank; and
(f) a computer interconnecting both said sensing means with both said pumps and arranged to control the pumps so that the feed rate of sugar solution and product discharge vary in accordance with yeast activity in said continuous fermenting tank so as to retain both the Baume and yeast cell count substantially constant in said tank during most of the time of fermentation.

The invention also includes a method which comprises controlling a pump to feed the sugar solution into a continuous fermenting tank, sensing the Baume and yeast concentration in the continuous fermenting tank, and effecting said control with a computer which interconnects Baume and yeast concentration sensors with said pump and is programmed to retain both Baume and yeast cell count substantially constant during most of the time of fermentation.

With the arrangement of the invention, it is possible to greatly reduce variations in the sugar content of the liquid in the continuous fermenting tank, (for example, by sensing change in the specific gravity) and also in yeast cell count, by pumping fresh sugar solution (for example, grape juice) into a tank as soon as reduction in Baume is sensed.

Since the control of the pumps is by way of a computer, they can clearly be controlled to run intermittently, but in a further embodiment of the invention, the sugar solution pump has a variable speed, and its variation of the output is controlled by the computer by varying pump speed.

The wide variations which will occur in the production of wine and certain other alcoholic beverages are most marked in the early stages of fermentation, and in a further embodiment of the invention there is provided a fermentation buffer tank and third pump which pumps from the continuous fermenting tank into the fermentation buffer tank, wherein, for example, fermentation will reduce Baume from about five to about three (or less as desired) before beverage is pumped from the fermentation buffer tank to storage means.

As is usual in fermenting tanks, all tanks can contain agitation means for retaining homogeneity of the biomass, and also release some of the carbon-dioxide which may otherwise dissolve.

If the biomass were to return into the conduit containing the fresh sugar solution the yeast contamination will occur, and in a further embodiment of the invention both the yeast from the yeast propagator and the sugar solution are delivered to the top of the continuous fermenting tank, and the output of the fermenting tank is delivered to the top of the fermentation buffer tank, the delivery conduits terminating above liquid level in those tanks thereby forming a syphon break and avoiding the possibility of flow back.

While it is possible for the tanks to be positioned at different levels, in this invention there is a positive control of the flow into and out of the continuous fermenting tank and the fermentation buffer tank, and in an embodiment there is provided a fourth pump connected to the fermentation buffer tank for delivery of beverage therefrom into storage means.

The importance of accurate control is not limited to the continuous fermenting tank, and in another embodiment there comprises both Baume sensing means and yeast concentration sensing means on the fermentation buffer tank, and the computer interconnects those sensing means and the fourth pump. Thus, neither of the continuous fermenting tank or fermentation buffer tank need necessarily always have a constant liquid level although this very desirable feature is normally maintained during fermentation.

Figure 2:
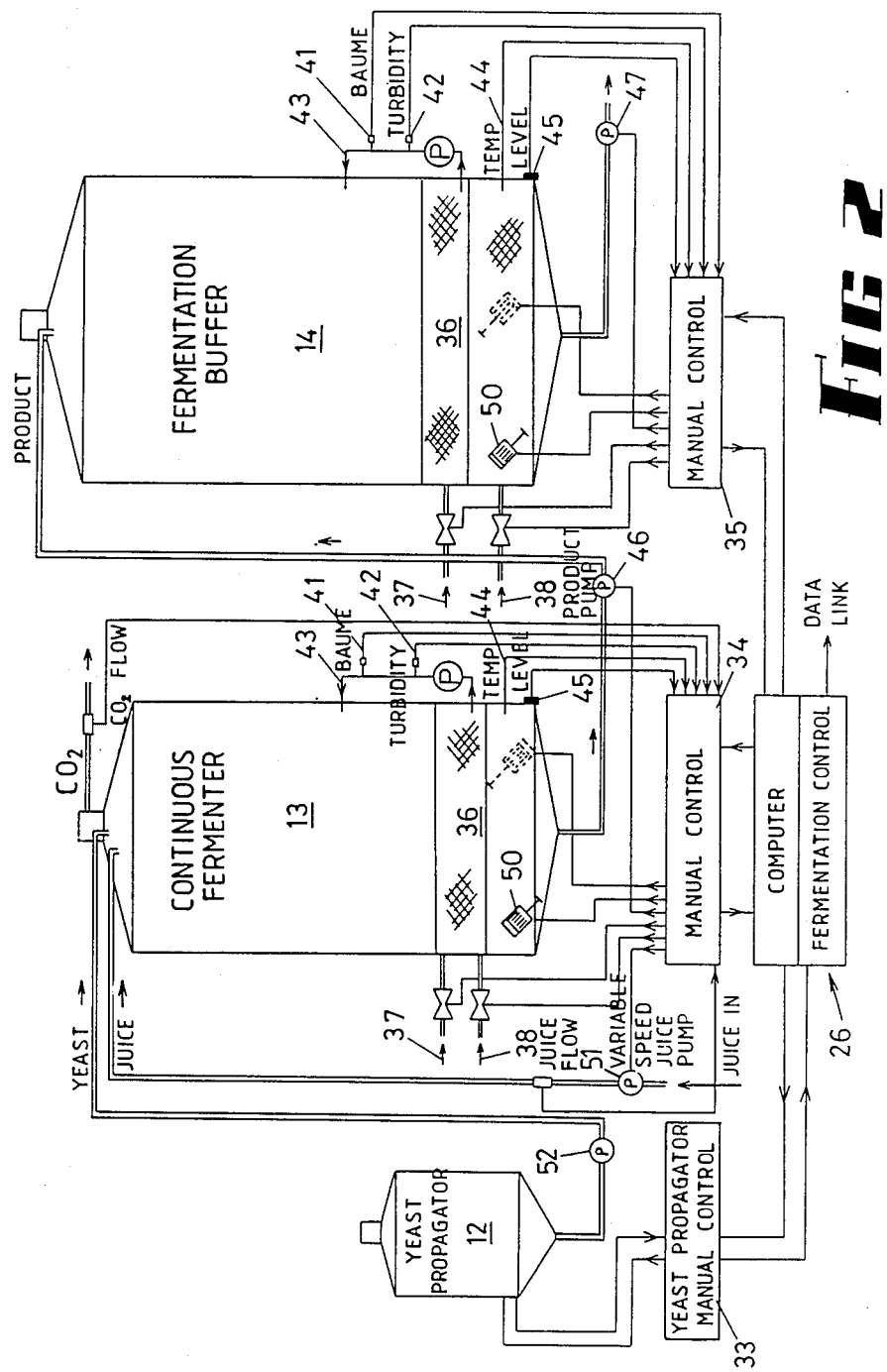

An embodiment of the invention is described hereunder in some detail with reference to and is illustrated in the accompanying drawings in which:

FIG. 1 shows diagrammatically an entire plan layout utilising the invention;

FIG. 2 shows in more detail a yeast propagator, continuous fermenting tank and fermentation buffer tank and the control means associated therewith; and FIG. 3 illustrates the volume and temperature within the continuous fermentation tank (hectalitres and degrees centigrade), the corresponding juice flow into the continuous fermenting tank (and also out of that into the fermentation buffer tanks) in hectalitres per hour and the yeast cell count, a percentage budding and Baume.

In this embodiment, as shown in FIG. 1 grape juice is pumped through a line 10 to a bacterial reactor 11, and separately to each of two yeast propagators 12, and separately into the continuous fermenting tank 13. The yeast propagator 12 functions identically to the continuous fermenting tank, but usually at a higher temperature to continuously breed yeast culture to provide a constant virulent innoculant (about $240 \times 10^6$ cell count per c.c.).

Control is effected by means of a computer the software of which is identified by the computer control diagram 16 which includes a 64 channel output 17 (D-A, A-D) the control programme 18 and the data acquisition interface 19. There is a manual control interface panel 20, and the control programme (responsive in a tank operating mode and also to the tank operating parameters) is controlled by an operator control keyboard 21, and its output includes a 40 column display 22 and also a video loop cable 23 for remote reading.

The computer used in this embodiment is a small "personal" computer sold under the trade mark APPLE, and utilises a hard 10 megabyte disc sold under the trade mark CORVUS and available from CORVUS SYSTEMS INC., San Jose, Calif., U.S.A. This is identified in the diagram by the designation 26, which also includes data acquisition storage and parameter files. It is associated with a data acquisition computer 22 which can not only store the data but can also provide a printed copy (hard copy) 28. The computer also controls the fermentation refrigeration 29, and the designations 30 and 31 relate to other on-line systems of use which are not relevant to this invention.

Reference is now made to FIG. 2 which shows diagrammatically the more specific subject matter of the invention. It illustrates a yeast propagator 12, the continuous fermenting tank 13 and the fermentation buffer tank 14. The capacity of the continuous fermenter 13 is such that continuing fermentation can take place for about twice a period of time as the Baume drops from about five to about three (or less as desired) in the fermentation buffer tank 14.

A manual control panel 33 will override the computer control for yeast propagator if necessary, the manual control panel merely consisting of a network of valves which are in accordance with known art. Similarly, the manual control panel 34 can override computer control for the continuous fermenting tank 13, and the panel 35 for the fermentation buffer tank 14.

When fermentation takes place in the continuous fermenter 13, the yeast cells will "bud", grow, split off and multiply in this way, sugar in the solution fed to the tank will be consumed, and the reaction is exothermic. The control of temperature in each tank is by respective heat exchangers 36 which are selectively fed by steam from a seam line 37 or chilled brine from a brine line 38. One of the problems which has been encountered heretofore with bud fermenting is that the initial temperature rise is very high, and it is necesary to have a large capacity refrigeration system, to avoid overheating the biomass, but in this invention the cell count does not exceed about $60 \times 10^6$, and Baume is maintained substantially constant for most of the initial stages of fermentation in tank 13, and this reduces peak load the refrigeration system.

In order to achieve the desired restriction of variation of cell count and Baume (FIG. 3) there is provided Baume sensing means 41 and turbidity sensing means 42 on each of the tanks 13 and 14, and this feeds data into the computer 26. The Baume sensing means is merely a specific gravity sensing means, and the turbidity sensing means 42 is a nephelometer sensor, manufactured in Australia by B.W.D. INSTRUMENTS PTY. LTD. of Melbourne. Although these two sensors are shown to exist in a branch loop line 43 this is not essential.

A temperature sensor 44 enters each respective tank 13 and 14, and a pressure transducer 45 senses level, it being desired for the level to remain constant. The respective output pumps 46 and 47 are controlled by the computer, and once the fermentation has settled down to become continuous (as shown on the heat count, bud and Baume graph of FIG. 3) the computer controls the pumps 46 and 47 to maintain constant level.

It has been believed heretofore that yeast propagation in a fermenting tank is a continuously increasing then declining activity as alcohol increases, but it has been discovered that this is not the case and, for example, the juice flow shown in FIG. 3 will be seen to peak periodically, indicating that yeast propagation is cyclic in its nature, yet it is desired that the cell count should remain substantially constant as shown also in FIG. 3. It is also to be noted from FIG. 3 that if the cell count is constant, the percentage of budding also remains constant. Therefore, the computer control functions between limits which are set both for Baume and the cell count, but under normal conditions the juice flow would be increased as shown in FIG. 3 at about the same time for each setting.

Juice flow rate is determined by either the cell density (per volume), or the sugar level (Baume). It is therefore the actual cell activity, in consuming sugar and constantly dividing itself into new cells, that sets the requirement for more juice. If the cells divide at a low rate then the juice feed is low, since an excess of juice will cause a dilution to occur, reducing the cell density below the set level.

An inherent capability of a computer is its ability to handle large volumes of numbers, to sort, modify, store and retrieve. In developing the process control systems previously described, a simple data acquisition structure was developed which is flexible and easy to programme and define. One inherent problem of storing data from a manufacturing process is the requirement to change the number or order of recorded items, and have compatibility with previous stored information.

The CORVUS hard disk which forms the network centre for the process control computers has an allocation of store space reserved for each process computer requiring data acquisition. This is organised as a 'recirculating memory' where the first data recorded is the first out if the storage space is filled. In this manner the most recent data is always retained and usually contains the last seven days of data.

Each process computer has a day/date/time list obtained by reading a 'time' file from the hard disk. (The time file is continually updated every minute from the Crusher Apple computer where a real time clock resides). According to the setting of an internal timer each control computer prints a list of data to its data acquisition file on the hard disk. This list consists of:

1. The total number of data records to be printed
2. The current day/date/time
3. The data list If at any time it is desired to change the number of recorded points, it is simply a matter of changing the number of recorded points index, then adding or subtracting the data points printed.

As is usual with fermenting tanks there are provided agitators 50 but it is important that these should be disconnected if the liquid levels drop, and this should therefore also be controlled via the computer. As liquid level lowers the agitators are switched off to avoid damage to the seals.

The first pump 51 which pumps juice into the continuous fermenting tank 13 can be controlled in intermittent mode by the computer, but in this embodiment is a variable speed pump which runs continuously but increases its speed upon increased demand for yeast or grape juice. Pump 52 can be dispensed with, since transfer of yeast from propagator 12 to continuous fermenting tank 13 seldom takes place, and can be done by hand (as at present).

The claims defining the invention are as follows:

1. Fermentation control means for controlling fermentation of sugar solution in the production of an alcoholic beverage, comprising:
   (a) a yeast propagating tank;
   (b) a continuous fermenting tank;
   (c) a first pump having an input conduit connected to a source of sugar solution and an output conduit connected to the continuous fermenting tank;
   (d) a second pump having an input conduit connected to an outlet of said continuous fermenting tank;
   (e) at least one of Baume sensing means and yeast concentration sensing means in communication with the contents of the continuous fermenting tank and both indirectly sensitive to yeast activity therein; and
   (f) a computer interconnecting said sensing means with both said pumps and arranged to control the pumps so that the feed rate of sugar solution and product discharge are controlled to vary in accordance with yeast activity in said continuous fermenting tank so as to retain both the Baume and yeast cell count substantially constant in said tank during most of the time of fermentation.

2. Fermentation control means according to claim 1 wherein each said pump has a variable output, and the variation of said output is controlled by said computer.

3. Fermentation control means according to claim 1 wherein the or each said Baume sensor is a specific gravity sensor.

4. Fermentation control means for controlling fermentation of sugar solution in the production of an alcoholic beverage, comprising:
   (a) a yeast propagating tank;
   (b) a continuous fermenting tank;
   (c) a fermentation buffer tank;
   (d) a first pump having an input conduit connected to a source of sugar solution and an output conduit connected to the continuous fermenting tank;
   (e) a second pump having an input conduit connected to an outlet of said continuous fermenting tank and an output conduit connected to said fermentation buffer tank;
   (f) at least one of Baume sensing means and yeast concentration sensing means in communication with the contents of the continuous fermenting tank and both indirectly sensitive to yeast activity therein; and
   (g) a computer interconnecting said sensing means with both said pumps and arranged to control the pumps so that the feed rate of sugar solution and product discharge are controlled to vary in accordance with yeast activity in said continuous fermenting tank so as to retain both the Baume and yeast cell count substantially constant in said tank during most of the time of fermentation.

5. Fermentation control means according to claim 4 wherein each said output conduit connects to its said tank near the upper end thereof, and terminates above liquid level therein.

6. Fermentation control means according to claim 5 comprising a third pump having an inlet conduit connected to said fermentation buffer tank, and an outlet conduit connected to storage means.

7. Fermentation control means according to claim 6 wherein said fermentation buffer tank also comprises Baume sensing means and yeast concentration sensing means, and said computer also connects those said sensing means and said third pump.

8. Fermentation control means according to claim 4 wherein both said continuous fermenting and fermentation buffer tanks have temperature sensing means and heat exchangers, and said computer so interconnects respective said temperature sensing means and heat exchangers as to open valves to said heat exchangers to in turn cause flow of heat exchange fluid therethrough so as to maintain temperature within said tanks in a narrow range.

9. Fermentation control means according to claim 4 further comprising agitators in both said continuous fermenting and fermentation buffer tanks, said agitators being effective for maintaining homogeneity and releasing carbon-dioxide gas from liquid in said tanks.

10. Fermentation control means according to claim 4 wherein each said pump has a variable output, and the variation of said output is controlled by said computer.

11. Fermentation control means according to claim 4 wherein the or each said Baume sensor is a specific gravity sensor.

12. Fermentation control means according to claim 4 wherein the or each said yeast concentration sensor is a light sensitive nephelometer which determines yeast cell count by sensing liquid turbidity.

13. Fermentation control means for controlling fermentation of sugar solution in the production of an alcoholic beverage, comprising:
   (a) a yeast propagating tank;
   (b) a continuous fermenting tank;
   (c) a first pump having an input conduit connected to a source of sugar solution and an output conduit connected to the continuous fermenting tank;
   (d) a second pump having an input conduit connected to an outlet of said continuous fermenting tank;
   (e) at least one of Baume sensing means and yeast concentration sensing means in communication with the contents of the continuous fermenting tank, and both indirectly sensitive to yeast activity therein, wherein the yeast concentration sensing means is a light sensitive nephelometer which determines yeast cell count by sensing liquid turbidity; and
   (f) a computer interconnecting said sensing means with both said pumps and arranged to control the pumps so that the feed rate of sugar solution and product discharge are controlled to vary in accordance with yeast activity in said continuous fermenting tank so as to retain both the Baume and yeast cell count substantially constant in said tank during most of the time of fermentation.

* * * * *